United States Patent [19]

Thomas, Jr. et al.

[11] 3,963,380
[45] June 15, 1976

[54] MICRO PUMP POWERED BY PIEZOELECTRIC DISK BENDERS

[76] Inventors: Lyell J. Thomas, Jr., 1900 Pelican Ave., San Pedro, Calif. 90731; Samuel P. Bessman, 2025 Zonal Ave., Los Angeles, Calif. 90033

[22] Filed: Jan. 6, 1975

[21] Appl. No.: 538,945

[52] U.S. Cl. ............................. 417/322; 417/412; 417/505; 128/1 D; 3/1.7
[51] Int. Cl.² .................. F04B 17/00; F04B 35/00; F04B 39/08; F04B 45/06
[58] Field of Search .......... 417/322, 317, 412, 413, 417/505, 518; 128/1 D; 3/1.7

[56] References Cited
UNITED STATES PATENTS

| | | | |
|---|---|---|---|
| 2,967,993 | 1/1961 | Eckerle et al. | 323/109 |
| 3,029,743 | 4/1962 | Johns | 417/322 |
| 3,215,078 | 11/1965 | Stec | 417/322 |
| 3,556,679 | 1/1971 | Middlebasher et al. | 417/317 |
| 3,735,245 | 5/1973 | Stigvils | 323/109 |
| 3,857,382 | 9/1973 | Williams et al. | 417/322 X |

OTHER PUBLICATIONS

The Piezoelectric Artificial Heart, Kosch et al., vol. X, Trans. Amer. Soc. Artif. Int. Organs, 1964, pp. 147–150.
Design of Piezoelectric Heart Assist Device, Williams et al., I.E.E.E. Transactions on Biomedical Engineering, vol. BME22, pp. 40–45, Jan. 1975.

*Primary Examiner*—William L. Freeh
*Assistant Examiner*—Richard E. Gluck
*Attorney, Agent, or Firm*—Fidelman, Wolffe & Waldron

[57] ABSTRACT

The pump has a piezoelectric variable volume chamber and a solenoid controlled valve operated in sequence to pump small volumes of liquid. The sequence is produced by developing a phase difference between the control of the piezoelectrical chamber and the solenoid valve.

11 Claims, 12 Drawing Figures

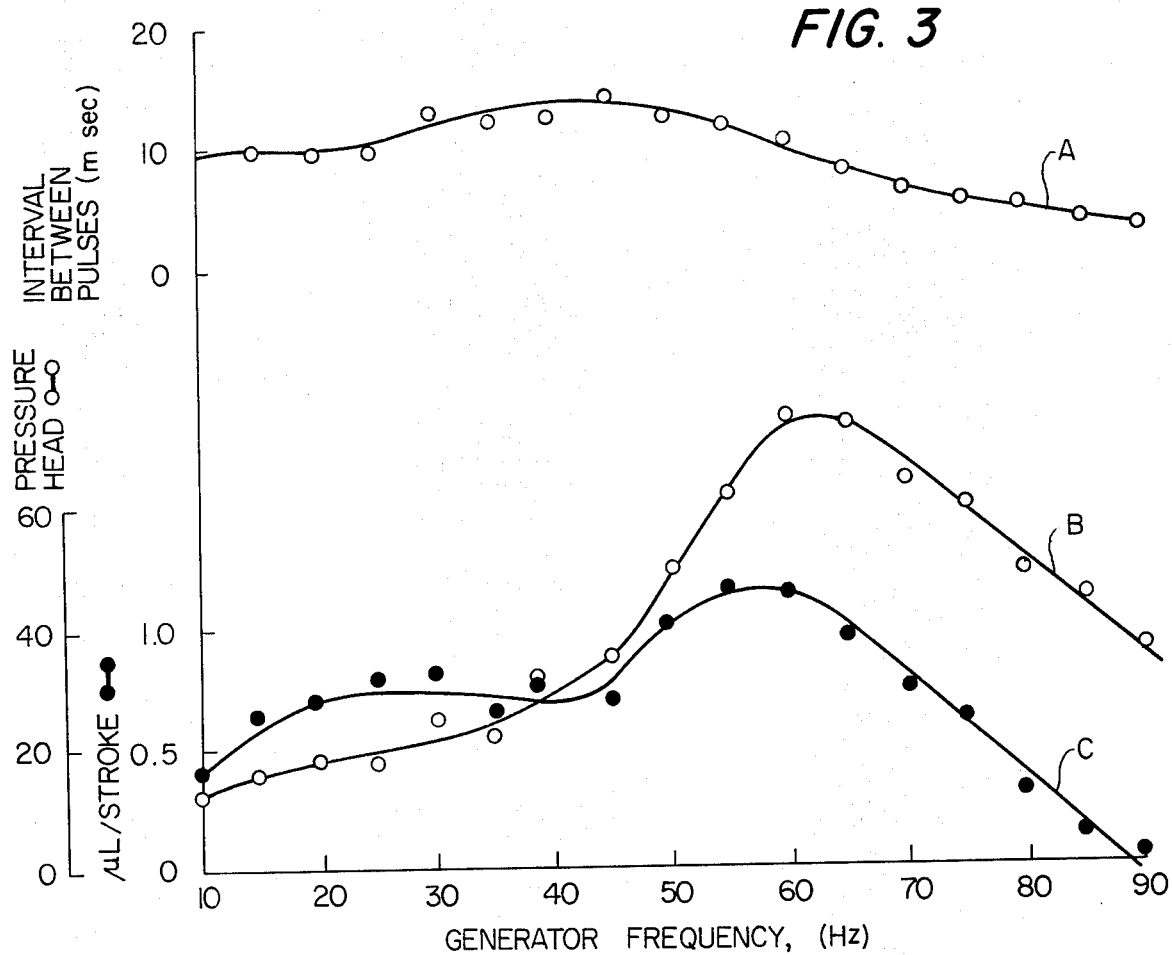
FIG. 3
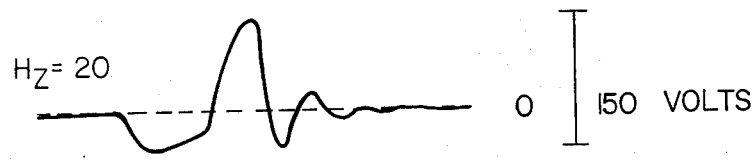
FIG. 4A
FIG. 4B
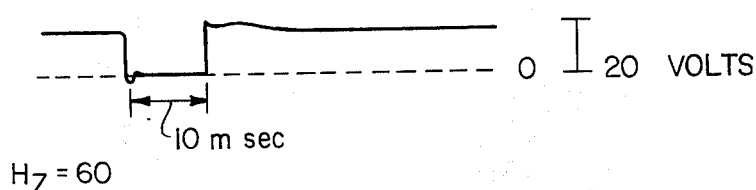
FIG. 4C
FIG. 4D

MICRO PUMP POWERED BY PIEZOELECTRIC DISK BENDERS

BACKGROUND OF THE INVENTION

1. Field of the Invention

The present invention relates generally to pumps and more specifically to a pump for implantation into the human body.

2. Description of the Prior Art

In the field of fluid delivery systems for use in the human body, the present devices are either not wholly implantable or the devices are not directly controllable or capable of preventing blow through caused by pressure applied to the inlet of the pump. The latter feature is necessary to insure that potentially dangerous overdoses of drugs or hormones are inadvertently forced into the host by sudden pressure on the reservoir, as might be caused by a blow. A miniature implantable roller type pump is described by G. D. Summers in "A New and Growing Family of Artificial Implanted Fluid Devices," *Am. Soc. Art. Int. Organs* 16: 219 (1970). This type of pump requires an extracorporeal power source which is supplied by an external motor magnetically coupled to the pump through the skin. Feedback control would require a rather complicated arrangement of the implanted and extracorporeal units. A fully implantable fluid delivery system is described by P. J. Blackshear et al., in "The Design and Initial Testing of an Implantable Infusion Pump," *Surgery, Gynecology and Obstetrics* 134: 51 (1972). It is powered by evaporation at a constant pressure of about ½ atmosphere of perfluoropentane isomers in an enclosed liquid-vapor system. A constant rate of outflow is maintained by a calibrated resistance in the outflow tube and by the viscosity of the delivered fluid. Feedback control in this system would require active valving of the outflow. But the lack of control over pumping pressure opens the possibility that the entire contents of the reservoir could empty into the host at a pressure of about 400mm Hg should the valve fail.

Both of the above described systems are capable of discrete quantitative delivery of aliquots of solution but each has serious drawbacks. There thus exists a need in the implantation field for a completely implantable fluid delivery system which is blow through proof, is susceptible to uncomplicated feedback control, is able to deliver discrete aliquots with reliability and requires sufficiently low power to permit a relatively long implantation life.

SUMMARY OF THE INVENTION

The problems of the prior art are solved by the miniature pump of the present invention which includes a variable volume chamber consisting of two apposed piezoelectric disk benders, forming a bellows, connected to a solenoid valve. A rectangular wave pulse generator directly activates the opening and closing of the solenoid valve and indirectly, through a step-up transformer, activates the flexing of the disk benders. This transformer provides a high voltage necessary for efficient operation of the disk benders. Also when properly activated by the pulse generator, the inductance of the secondary winding of this transformer, the resistance of the winding, and the capacitance of the disk benders, act as a phase shift network to provide the desired relationship between pump stroke and valve opening. The volume delivery per stroke of the pump can be under 0.2 microliters and the total delivery is a function of the number of pulses from the generator. Optimum performance is achieved by setting the frequency of the pulse generator to the hydrodynamic resonant frequency of the fluid system and setting the duration of the pulse so as to achieve proper phasing between motion of disk benders and valve.

OBJECTS OF THE INVENTION

The principal objective of the present invention is to provide a pump for a controllable fluid delivery system which can be made completely implantable. To accomplish this, it was necessary for the present invention to achieve the following objects:

1. capability for simple control of output to permit reliable feedback regulation;
2. ability to deliver extremely small volumes without employing small precision parts so that the pump can perform over long periods without failure;
3. low power consumption to permit long duration of function from implanted batteries;
4. small size to permit incorporation into a complete system of sensors, amplifiers, power supply, etc.
5. A valving arrangement such that it is not possible to force fluid through the pump when the pump is not active.

Other objects, advantages and novel features of the present invention will become apparent from the following detailed description of the invention when considered in conjunction with the accompanying drawings.

BRIEF DESCRIPTION OF THE FIGURES

FIG. 3 is a plot of data from a working pump showing the following as a function of driving frequency from the rectangular wave generator: curve A) optimum interval (milliseconds) between pulses to obtain maximum output pressure at a given frequency (Hz); curve B) maximum output pressure (mm Hg) obtainable at a given frequency (Hz); and curve C) maximum output volume per stroke (microliters) obtainable at a given frequency (Hz). This was obtained with resistance to outflow reduced to a minimum;

FIGS. 4A and 4B are wave forms of the voltage across the transformer secondary winding and the voltages across the output of the rectangular wave generator, respectively, at 20Hz. FIGS. 4C and 4D are wave forms of the voltage across the transformer secondary winding and the voltage across the output of the rectangular wave generator, respectively, at 60Hz;

DESCRIPTION OF THE PREFERRED EMBODIMENTS

Figures 1A, 1B:
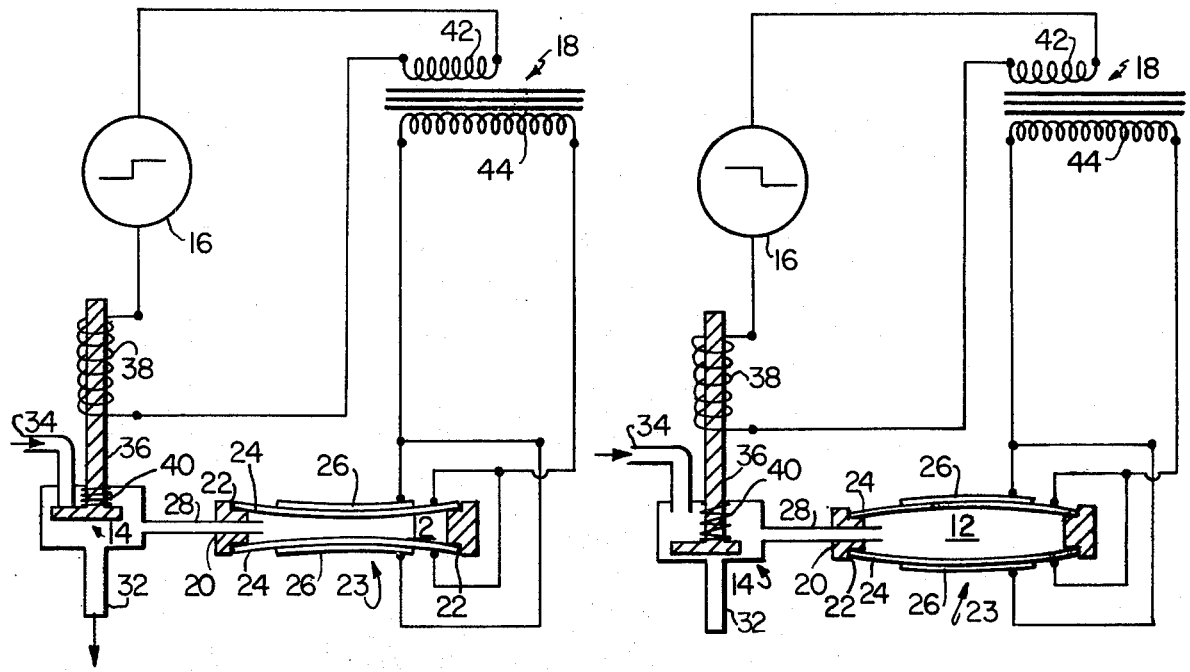
FIGS. 1A and 1B are schematics of a preferred embodiment of the present invention in an exhaust stroke and in an intake stroke, respectively.

FIG. 1 illustrates a preferred embodiment of the pump with the variable volume chamber 12, a solenoid controlled valve 14, a rectangular wave generator 16 and a transformer 18. The variable volume chamber 12 includes a cylindrical section 20 having a pair of internal shoulders 22. Resting on the shoulders 22 and forming the remainder of the chamber are a pair of disk benders 23 which change their shape in response to an electrical signal. This cylindrical element 20 may be made of plastic, for example Lexan, and the disk bender may be a commercially available unit, for example, disk bender type G-1500, available from Gulton Industries, Fullerton, Ca. The disk benders are secured to the cylindrical element 20 by contact cement, for example, Eastman 910. The disk benders consist of a thin wafer (0.009 inch thick and 0.980 inch in diameter) of piezoelectrical material (lead zirconate-titanate piezoceramic) bonded with epoxy cement to a slightly larger disk 24 of brass shim stock (0.10 inch thick and 1.375 inch in diameter). The outer surface of the wafer has a thin layer of silver deposited thereon. Electrical connections are made by soldering to this layer of silver and to the brass disk.

When voltage is supplied between the silver film and the brass disk, the resulting electrical field set up within the crystal causes it to expand or shrink in diameter, depending upon the direction of the applied voltage. However, since the circumference of the crystal cannot increase because of the bonding to the brass disk, the resulting motion is that of bulging in the center to form a spherical surface. The magnitude of the change is proportional to the applied voltage. The variable volume chamber 12 is connected to solenoid valve 14 by a conduit 28 which is received within an aperture 30 in the wall 20. The valve 14 has an outlet 32 and an inlet 34. The fluid communication of conduit 28 and the variable volume chamber 12 to inlet 34 and outlet 32 is controlled by armature 36 of solenoid 38. It should be noted that the armature 36 is held in a closed position, when the solenoid 38 is deactivated, by a spring 40. The inlet 34 is connected to a reservoir containing the fluid to be dispensed and outlet 32 is connected to the portion of the body to receive the fluid. As shown in FIG. 1A, the valve allows communication between the variable volume chamber 12 and the outlet 32; whereas, in FIG. 1B, the fluid in the valve communicates with the reservoir through inlet 34 and the variable volume chamber 12. The solenoid valve 14 may be a miniature valve, catalog No. L.I.F. 180D3C12, available from the Lee Company, Westbrook, Conn.

The coil of the solenoid 38 is connected in series with the rectangular wave generator 16 and the primary winding 42 of the transformer 18 as shown in FIGS. 1A and 1B. The secondary winding 44 of the transformer 18 is connected to the pair of piezoelectric crystals 26 and the brass disks 24. These connections to the disk benders are such that they move towards or away from each other in response to a positive or negative voltage. The secondary winding 44 of the transformer 18 provides a high voltage necessary for efficient deformation of the piezoelectric wafers 26 and is also an integral part of the phase shift network responsible for proper sequencing of the fluid pulses in and out of the variable volume chamber 12 and opening and closing of the solenoid valve 14. This phase shift network consists of the inductance and resistance of the secondary winding 44 of the transformer connected in series with the capacitance of the wafers of piezoelectric material. These values appear to be fairly critical and, in the present embodiment of the pump, the transformer secondary winding DC resistance was 6750 Ω with an inductance of about 500 Milli Henrys and the combined capacitance of the two disk benders was about 0.04 microfarads. The transformer 18 may be a pair of miniature audio input types such as Allied Electronics, Archer catalogue No. 273-1376 connected in series. The disk benders are connected to the high impedance windings and the solenoid valve and rectangular wave generator are connected to the low impedance windings. The rectangular wave pulse generator may be a semiconductor integrated circuit such as MC1455 made by Motorola. Though a specific pulse generator is disclosed, it should be noted that this may be any other type of device which provides a periodic positive or negative rectangular wave voltage pulse with sufficient power and which can be accurately regulated as to frequency and pulse Duration in the frequency range of about 10 to 100 Hz. It is important to note that this voltage pulse may be either positive or negative during a single cycle, but not both in sequence. Otherwise the solenoid valve would remain open all the time as if operated by conventional alternating current. The signal generator 16 may provide continuous periodic pulses to operate the pump continuously or may provide a fixed number of pulses for intermittent operation of the pump.

As illustrated in FIG. 1A, in response to a pulse of one polarity (positive), the solenoid 38 is activated to retract plunger 36 against spring 40 to open the outlet 32 and close the inlet 34. At the same time, as shown in FIG. 1A, the variable volume chamber 12 begins to expel some of its contents because the voltage induced in the secondary 44 of the transformer makes the disk benders 23 start to flex inward. As shown in FIG. 1B, the current flow from the pulse generator stops suddenly at the end of the rectangular wave pulse. This deactivates the solenoid 38 and allows spring 40 to return the armature 36 to its extended position opening inlet 34 and closing outlet 32. Also, this sudden cessation of current flow through the primary 42 of transformer 18 induces a large voltage in the secondary 44 which has a polarity opposite to that of the preceding half cycle. This causes the disk benders 23 to flex in the opposite direction (outward) so that fluid is drawn into the variable volume chamber from the reservoir.

The potential for long life and reliability in a pump of this design can be judged by the following:

1. The force doing useful work is developed electrostatically within a crystal. No bearings or sliding parts are required in the variable volume chamber so that frictional wear is essentially eliminated in this part of the pump;

2. The requirements for the solenoid valve are not critical since its only function is to open and close and it does not participate in metering the amount of fluid delivered. The manufacturer of the valve currently used states that "testing shows an operating life of at least 200 million cycles";

3. Because there is no requirement for closely fitted parts anywhere in this pump, the danger of clogging by detritus in the pumped fluid is minimal.

4. Since the solenoid valve is spring biased closed to the outlet, it is impossible for fluid to pass from the reservoir to host except when the pump is active. This is an essential safety feature of the device and cannot be achieved by any type of passive valving system.

Figure 2A:
FIGS. 2A, 2B and 2C are tracings from an oscilloscope record showing simultaneous display of A (voltage from the signal generator; B) voltage applied to the piezoelectric elements, and C) isometric pressure (mm Hg) in the variable volume chamber.
Figure 2B:
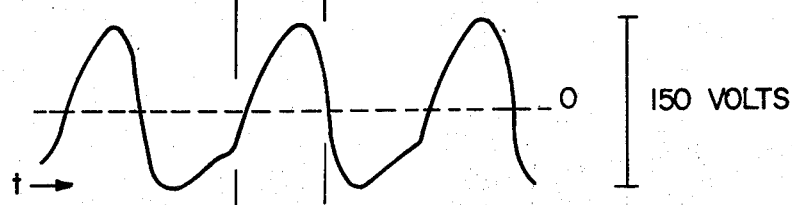
Figure 2C:
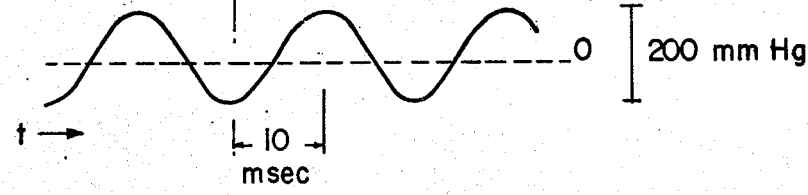

FIG. 2 is a tracing of an oscilloscope record showing the relationships of the wave forms from the signal generator (FIG. 2A), voltage across the disk bender 23 (FIG. 2B), and the pressure in the variable chamber (FIG. 2C). The horizontal scale is time in milliseconds and the dotted lines indicate zero voltage and pressure levels. This and subsequent measurements were recorded from Tektronix type 551 dual beam oscilloscope with a Polaroid camera. One side of the oscilloscope was equipped with a type CA beam splitting unit to record the two voltages and the other side was equipped with a type Q transducer coupling unit connected to a Statham P23BB pressure transducer. The rectangular wave generator used to obtain the subsequent data, because of its great flexibility, was a Grass S 4 G Physiological Stimulator. In order to construct a device of implantable size, we have used a microcircuit timing device, MC1455 by Motorola. But, as noted previously, any device providing the proper wave form and power could be used.

FIG. 2A shows the rectangular wave from the generator 16 having alternative positive and zero voltage levels. The solenoid 14 is activated during the positive voltages so as to connect outlet 32 and the variable volume chamber 12 and is deactivated during the zero level signals to connect the inlet 34 and the variable volume chamber 12. The voltage across the disk benders 23 originating in the secondary 44 of transformer 18 is shown in FIG. 2B to be approximately sinussodial with peaks that lag the beginning and end of the rectangular wave from the generator. This is the optimum condition for operation of the pump but this wave form varies considerably if frequency or duration of the rectangular pulse are changed or if the inductance, resistance or capacitance in the secondary circuit of the transformer are changed. This is discussed below in connection with FIGS. 3 and 4. The desired time delay between the rising edge of the rectangular wave from the generator 16 and peak voltage across the bender disks 23 is approximately equal to the duration of the rectangular wave. The reason for this can be seen by reference to FIG. 2. The opening and closing of the solenoid valve approximately coincide with the beginning and end of the square wave shown in FIG. 2A. The pressure developed in the variable volume chamber 12 shown in FIG. 2C approximately coincides with the voltage across the disk bender as shown in FIG. 2B. Therefore, this relationship permits the variable volume chamber 12 to deliver a maximum amount of fluid through outlet 32 during the time that the valve 14 is open to the outlet and to take in a maximum amount of fluid through inlet 34 when the valve is open to the inlet.

FIG. 3 shows that the frequency and duration of the rectangular wave pulse from the signal generator are critical factors in obtaining optimum performance from the pump. These data were obtained using a voltage of 25 volts from the generator by determining the optimum duration of rectangular wave (designated as interval between pulses) at a given frequency (curve 3A) needed to obtain maximum output pressure (outflow completely restricted) at this frequency (curve 3B). The output volume per stroke which could be obtained under these conditions with resistance to flow removed (zero pressure head) is shown in curve 3C. It is seen that the maximum pressure and outflow were obtained in the vicinity of 60Hz with each falling off rather rapidly on either side of this frequency. It is also seen from curve A that the interval between pulses to give optimum performance at any frequency is practically constant. The reasons for this latter phenomenon can be explained by reference to FIG. 4.

The voltage wave form across the disk benders and transformer secondary is shown at 20Hz in FIG. 4A, curves A and B, and at 60Hz in FIG. 4B, curves C and D, with 20 volts supplied by the rectangular wave generator in each case. First of all, it is seen that the peak to peak voltage across the bender is about 200 V at 60Hz but only about 150 V at 20Hz. The reason for this is that, at the lower frequency, much of this voltage is dissipated in useless oscillations whereas at the optimum frequency these oscillations become additive and the system resonates. This permits a maximum in and out movement of the benders with a minimum of expenditure of energy. The reason for the relationship seen in curve A of FIG. 3 appears to be that the wave form induced by the collapse of the field in the transformer secondary during an approximate 10 millisecond interval is optimal at all frequencies. It will be recalled from FIG. 1B that during this part of the cycle the pump fills.

Figure 5:
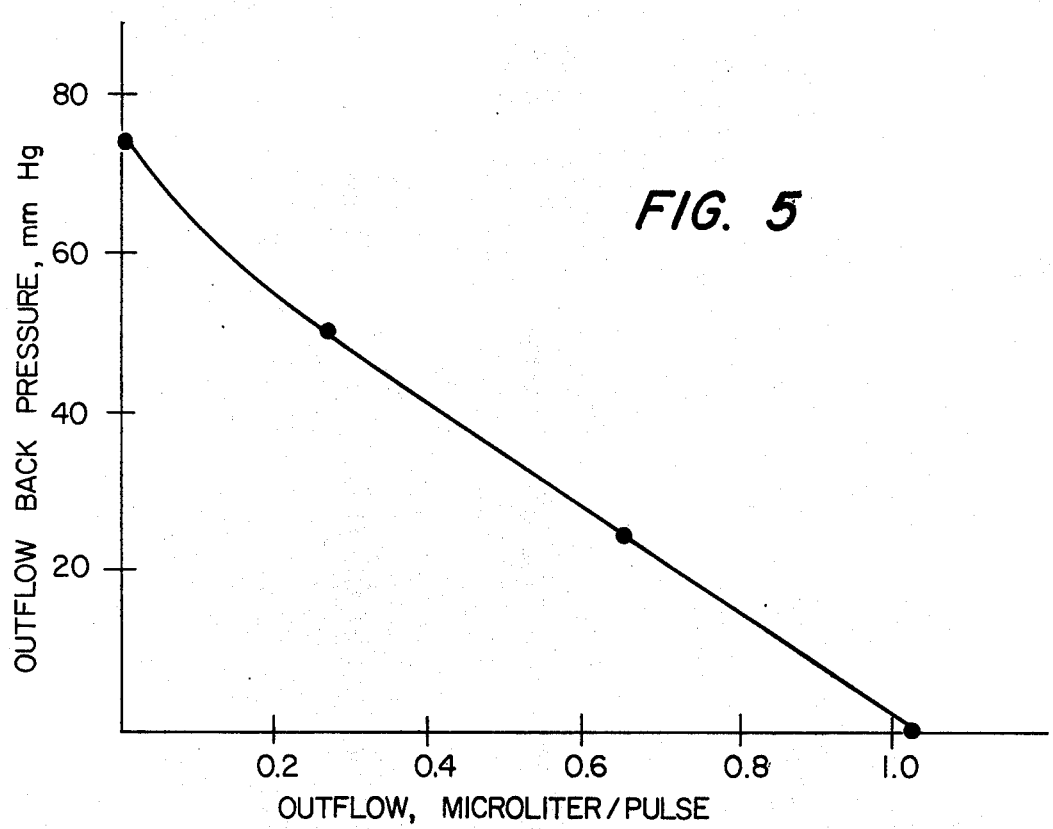
FIG. 5 is a plot of data from a working pump showing output volume in microliters per pulse (horizontal scale) as a function of back pressure in mm Hg developed against a resistance to outflow.

From the foregoing, it appears that the optimum performance of the pump is achieved when it puts out a train of pulses at resonance. Control of output can be achieved by either regulating the duration of a single train of pulses or by increasing or decreasing the number of identical trains of pulses in a given time interval. The latter is to be preferred, since due to elasticity of the components in the system, a finite number of pulses are required to attain a constant pressure head. In the latter case, it is not necessary that maximum output pressure be delivered during a pulse train since identical trains produce the the same end output pressure over the same time course and hence deliver the same final volume per train. In the present system, a pressure of about 40mm Hg developed after 10 optimal pulses with outflow completely restricted. When the restrictive resistance was reduced so that the pressure rose to only 20mm Hg, the fluid output during the 10 pulses was 5 ± 0.2 micro liters. This use of a restrictive resistance would be of no value as a variable adjustment, but is of great value in setting the maximum rate of output. FIG. 5 shows that the relationship between pressure developed against a resistance to flow (outflow back pressure) and outflow is linear. From this figure, it can be seen that a useful output as small as 0.2 microliters or less per pulse can be achieved by employing a resistance to outflow.

Figure 6:
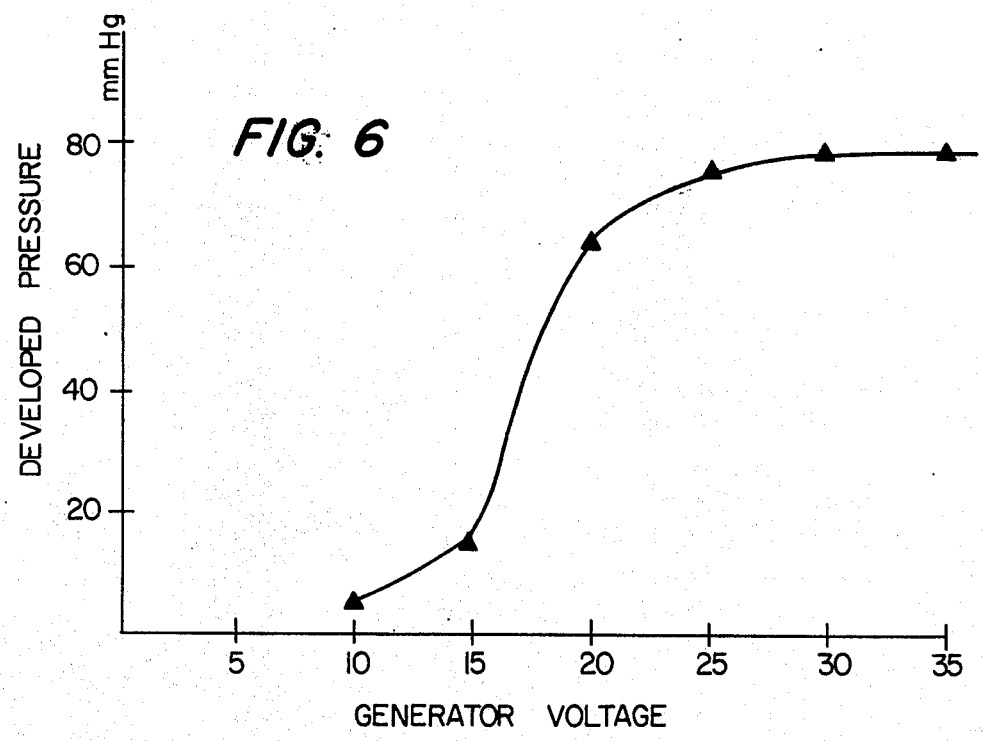
FIG. 6 is a plot of data from a working pump showing maximum output pressure (mm Hg) of the pump as a function of rectangular wave generator voltage.

In addition to the means for regulating output discussed above, control of the delivery voltage is another possibility. FIG. 6 shows that the maximum developed pressure vs. generator voltage is linear over part of the working range. However, it is equally interesting that there appears to be an absolute maximum pressure which the system can develop. In the case shown here, it was 80mm Hg, but with other variable volume chambers, this pressure has been as high 120mm Hg. This fact could be used to advantage to buffer the pump against variations in output resulting from variations in delivery voltage.

The power consumption of the pump was measured under the optimum conditions shown in FIG. 4D and the energy consumed per pulse can be calculated from the following: Duration of the 20 volt square wave pulse was 6 milliseconds. The current was measured with a Hewlett Packard model 428B Clip-on D.C. milliameter connected to one channel of the oscilloscope and found to be 7.5 milliamperes during this 6 millisecond pulse. Thus, energy consumption is about $20 \times 7.5 \times 6 \times 10^{-6} – 10^{-3}$ joules per pulse. If the pump were operated as described in the preceding paragraph (trains of 10 pulses delivering 5 microliters per train), the energy consumption per microliter delivered would be $2 \times 10^{-3}$ joules. Now a typical one ampere hour mercury cell of the type used in implanted cardiac pacemakers has an energy content of about $4.8 \times 10^3$ joules. Assuming half of this energy to be available for useful work, the pump could deliver about one liter from this power source.

If the present system were used to dispense insulin based on a need of 0.15 milliliters per day, it would take 18 years for the present pump to pump one liter. This figure, that is, 18 years, must be diminished by the shelf life of the battery. It should be noted that 0.15 milliliter per day requirement of insulin at 100 units ml described by Dr. S. P. Bessman in "Diabetes Mellitus: Observations, Theoretical and Practical," *J. Ped* 56: 191 (1960). The present apparatus has been built to operate by batteries and occupy less than 50 milliliters of volume.

Although the preferred embodiment has been described in detail using specific commercially available components, these are but examples of piezoelectric elements, electrically operated valves, signal generators and phase shifting circuits. The spirit and scope of this invention are to be limited only by the terms of the appended claims.

What is claimed:

1. A pump having an inlet and an outlet comprising:
a variable volume chamber having a single port and at least one piezoelectric wall;
a single solenoid valve for controlling the communication of said port to said inlet and outlet;
a signal generator; and
a transformer having said solenoid valve and said signal generator connected in series on one side of the transformer and said piezoelectric wall connected to the other side of the transformer;
the sequential operation of said solenoid valve and said piezoelectric wall needed to produce a pumping effect being produced by the electrical characteristics of the transformer, solenoid valve and piezoelectric wall.

2. The pump of claim 1 wherein said transformer is a step up transformer and said signal generator and said solenoid valve are connected on the primary and said piezoelectric wall is connected on the secondary.

3. The pump of claim 1 wherein said chamber is founded by two piezoelectric elements, each forming a wall of said chamber.

4. The pump of claim 1 wherein said solenoid valve includes an armature movable between said inlet and said outlet and biasing means for urging said armature to close said outlet.

5. A pump having an inlet and an outlet comprising:
a chamber means for holding a medium being pumped and having a port;
a piezoelectric means connected to said chamber means for varying the volume of said chamber means;
a solenoid valve connected between said inlet, said outlet and said port for controlling the communication of said port with said inlet and said outlet; and
control means connected to said piezoelectric means and said solenoid valve for electrically activating said piezoelectric means and said solenoid valve in a desired sequence to move said medium from said inlet to said chamber means and from said chamber means to said outlet, past said solenoid valve.

6. The pump of claim 5 wherein said solenoid valve includes an armature movable between said inlet and said outlet and biasing means for urging said armature to close said outlet.

7. The pump of claim 5 wherein said control means includes an oscillator means providing an electric signal of a selectively fixed frequency and the volume of delivery of said pump being proportional to the said selected frequency of said electrical signal of said oscillator means.

8. The pump of claim 7 wherein said frequency is the resonant frequency of said, piezoelectric means.

9. The pump of claim 5 wherein said control means includes an oscillator means for providing periodic voltages, and a transformer, said piezoelectric means being connected across the secondary of said transformer and said solenoid valve being connected in series with said oscillator means across the primary of said transformer, said transformer providing the required sequencing of said piezoelectric means and said solenoid valve.

10. The pump of claim 5 wherein said piezoelectric means is operable for the pump to deliver less than 0.2 microliters per stroke.

11. The pump of claim 5 wherein said chamber means is bounded by said piezoelectric means, said last means being two piezoelectric elements, each forming a wall of said chamber means.

* * * * *